(12) United States Patent
Linscombe

(10) Patent No.: US 7,253,347 B2
(45) Date of Patent: Aug. 7, 2007

(54) RICE CULTIVAR DESIGNATED 'TRENASSE'

(75) Inventor: Steven D. Linscombe, Crowley, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 11/232,493

(22) Filed: Sep. 21, 2005

(65) Prior Publication Data

US 2007/0067863 A1    Mar. 22, 2007

(51) Int. Cl.
*A01H 5/00* (2006.01)
*A01H 5/10* (2006.01)
*A01H 4/00* (2006.01)
*A01H 1/00* (2006.01)
*C12N 15/82* (2006.01)

(52) U.S. Cl. .................. 800/320.2; 800/260; 800/279; 800/281; 800/284; 800/300; 800/301; 800/302; 435/410

(58) Field of Classification Search ................ 800/260, 800/279, 281, 284, 300, 301, 302, 320.2; 435/410
See application file for complete search history.

(56) References Cited

FOREIGN PATENT DOCUMENTS

| | | |
|---|---|---|
| WO | WO 00/27182 | 5/2000 |
| WO | WO 01/85970 | 11/2001 |

OTHER PUBLICATIONS

Gravois, K.A. et al., "Registration of Cultivars (Registration of 'Kaybonnet' Rice)," Crop Science, vol. 35, pp. 587-588 (1995).
95th Annual Report, Rice Research Station 2003 (published in 2004).
96th Annual Report, Rice Research Station 2004 (published in 2005).
Kuenzel, K.A. et al., Registration of 'Tebonnet' Rice, Crop Science, vol. 25, pp. 1126-1127 (1985).
Linscombe, S.D., et al., Registration of 'Cypress' Rice, Crop Science, vol. 33, p. 355 (1993).
Tseng, S.T. et al., Registration of L-202 Rice, Crop Science, vol. 24, pp. 1213-1214 (1984).
Xie, Q.J. et al., Registration of LSBR-33 and LSBR-5 Sheath Blight-Resistant Germplasm Lines of Rice, Crop Science, vol. 32, p. 507 (1992).

*Primary Examiner*—David H. Kruse
*Assistant Examiner*—Keith O. Robinson
(74) *Attorney, Agent, or Firm*—John H. Runnels; Bonnie J. Davis

(57) ABSTRACT

A novel rice cultivar, designated 'Trenasse,' is disclosed. The invention relates to the seeds of rice cultivar 'Trenasse,' to the plants of rice 'Trenasse,' and to methods for producing a rice plant produced by crossing the cultivar 'Trenasse' with itself or another rice variety, and to single gene conversions of such plants. The invention further relates to hybrid rice seeds and plants produced by crossing the cultivar 'Trenasse' with another rice cultivar.

23 Claims, No Drawings

RICE CULTIVAR DESIGNATED 'TRENASSE'

This invention pertains to a new and distinct rice cultivar, designated 'Trenasse.'

Rice is an ancient agricultural crop, and is one of the principal food crops of the world. There are two cultivated species of rice: *Oryza sativa* L., the Asian rice, and *O. glaberrima* Steud., the African rice. *Oryza sativa* L. constitutes virtually all of the world's cultivated rice and is the species grown in the United States. Three major rice-producing regions exist in the United States: the Mississippi Delta (Arkansas, Mississippi, northeast Louisiana, southeast Missouri), the Gulf Coast (southwest Louisiana, southeast Texas), and the Central Valley of California. See generally U.S. Pat. No. 6,911,589.

Rice is a semiaquatic crop that benefits from flooded soil conditions during part or all of the growing season. In the United States, rice is typically grown on flooded soil to optimize grain yields. Heavy clay soils or silt loam soils with hard pan layers about 30 cm below the surface are typical rice-producing soils because they reduce water loss from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination comes from irrigation or rainfall. Another method of dry-seeding is to broadcast the seed by airplane into a flooded field, and then to promptly drain the water from the field. For the dry-seeded system, when the plants have reached sufficient size (four- to five-leaf stage), a shallow permanent flood of water 5 to 16 cm deep is applied to the field for the remainder of the crop season.

One method of water-seeding is to soak rice seed for 12 to 36 hours to initiate germination, and then to broadcast the seed by airplane into a flooded field. The seedlings emerge through a shallow flood, or the water may be drained from the field for a short period of time to enhance seedling establishment. A shallow flood is then maintained until the rice approaches maturity. For both the dry-seeded and water-seeded production systems, the fields are drained when the crop is mature, and the rice is harvested 2 to 3 weeks later with large combines.

In rice breeding programs, breeders typically use the same production systems that predominate in the region. Thus, a drill-seeded breeding nursery is typically used by breeders in a region where rice is drill-seeded, and a water-seeded nursery is used in regions where water-seeding prevails.

Rice in the United States is classified into three primary market types by grain size and shape, and composition of the endosperm: long-grain; medium grain; and short-grain. Typical U.S. long-grain cultivars cook dry and fluffy when steamed or boiled, whereas medium- and short-grain cultivars cook moist and sticky. Long-grain cultivars have been traditionally grown in the southern states and generally receive higher market prices.

Although specific breeding objectives vary somewhat in different regions, increasing yield is a primary objective in all programs. Grain yield depends, in part, on the number of panicles per unit area, the number of fertile florets per panicle, and grain weight per floret. Increases in any or all of these components may help improve yields. Heritable variation exists for each of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics on grain quality.

Choice of breeding or selection methods depends on the mode of plant reproduction, the heritability of the trait(s) being improved, and the type of cultivar used commercially (e.g., $F_1$ hybrid cultivar, versus pure line or inbred cultivars). For highly heritable traits, a choice of superior individual plants evaluated at a single location may sometimes be effective, while for traits with low or more complex heritability, selection is often based on mean values obtained from replicated evaluations of families of related plants. Selection methods include pedigree selection, modified pedigree selection, mass selection, recurrent selection, and combinations of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s), typically for three or more years. The best lines become candidates for new commercial cultivars; those still deficient in a few traits may be used as parents to produce new populations for further selection.

These processes, which lead ultimately to marketing and distribution of new cultivars or hybrids, typically take 8 to 12 years from the time of the first cross; they may further rely on (and be delayed by) the development of improved breeding lines as precursors. Development of new cultivars and hybrids is a time-consuming process that requires precise forward planning and efficient use of resources, with no assurances that there will ever be a successful outcome.

A particularly difficult task is the identification of individual plants that are, indeed, genetically superior. A plant's phenotype results from a complex interaction of genetics and environment. One method for identifying a genetically superior plant is to observe its performance relative to other experimental plants and to a widely grown standard cultivar raised in an identical environment. Repeated observations from multiple locations can help provide a better estimate of its genetic worth.

The goal of rice breeding is to develop new, unique, and superior rice cultivars and hybrids. The breeder initially selects and crosses two or more parental lines, followed by self pollination and selection, producing many new genetic combinations. The breeder can generate billions of different genetic combinations via crossing, selfing, and mutation breeding. The breeder has no direct control at the cellular level. Therefore, two breeders working independently of one another will never develop the same line, or even very similar lines, with the same traits.

Each year, the plant breeder selects germplasm to advance to the next generation. This germplasm is grown under different geographical, climatic, and soil conditions. Further selections are then made, during and at the end of the growing season. The resulting cultivars (or hybrids) and their characteristics are inherently unpredictable. This is because the breeder's selection occurs in unique environments, with no control at the genetic level (using conventional breeding procedures), and with potentially billions of different possible genetic combinations being generated. A breeder cannot predict the final resulting line, except possibly in a very gross and generic fashion. Further, the same breeder may not produce the same cultivar twice, even starting with the same parental lines, using the same selection techniques. This unpredictability results in substantial effort and expenditures in developing superior new rice cultivars.

The selection of superior hybrid crosses is conducted slightly differently. Hybrid seed is typically produced by manual crosses between selected male-fertile parents or by using genetic male sterility systems. These hybrids are typically selected for single gene traits that unambiguously indicate that a plant is indeed an $F_1$ hybrid that has inherited traits from both presumptive parents, particularly the male parent (since rice normally self-fertilizes). Such traits might include, for example, a semi dwarf plant type, pubescence, awns, or apiculus color. Additional data on parental lines, as well as the phenotype of the hybrid, influence the breeder's decision whether to continue with a particular hybrid cross or an analogous cross, using related parental lines.

Pedigree breeding and recurrent selection breeding methods are sometimes used to develop cultivars from breeding populations. These breeding methods combine desirable traits from two or more cultivars, or other germplasm sources into breeding pools from which cultivars are developed by selfing and selection of desired phenotypes. The new cultivars are evaluated to determine commercial potential.

Pedigree breeding is often used to improve self-pollinating crops. Two parents possessing favorable, complementary traits are crossed to produce $F_1$ plants. An $F_2$ population is produced by selfing one or more $F_1$s. Selection of the superior individual plants may begin in the $F_2$ (or later) population. Then, beginning in the $F_3$ (or other subsequent) generation, individual plants are selected. Replicated testing of panicle rows from the selected plants can begin in the $F_4$ (or other subsequent) generation, both to fix the desired traits and to improve the effectiveness of selection for traits that have low heritability. At an advanced stage of inbreeding (e.g., $F_6$ or $F_7$), the best lines or mixtures of phenotypically-similar lines are tested for potential release as new cultivars.

Mass and recurrent selection methods can also be used to improve populations of either self- or cross-pollinating crops. A genetically variable population of heterozygous individuals is either identified or created by intercrossing several different parents. The best offspring plants are selected based on individual superiority, outstanding progeny, or excellent combining ability. The selected plants are intercrossed to produce a new population in which further cycles of selection are continued.

Backcross breeding is often used to transfer genes for a simply inherited, highly heritable trait into a desirable homozygous cultivar or inbred line, which is the recurrent parent. The source of the trait to be transferred is called the donor parent. The resulting plant should ideally have the attributes of the recurrent parent (e.g., cultivar) and the desired new trait transferred from the donor parent. After the initial cross, individuals possessing the desired donor phenotype (e.g., disease resistance, insect resistance, herbicide tolerance) are selected and repeatedly crossed (backcrossed) to the recurrent parent.

The single-seed descent procedure in the strict sense refers to planting a segregating population, harvesting a sample of one seed per plant, and using the one-seed sample to plant the next generation. When the population has been advanced from the $F_2$ generation to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, the breeder harvests one or more seeds from each plant in a population and threshes them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh panicles by machine than to remove one seed from each by hand as in the single-seed procedure. The multiple-seed procedure also makes it possible to plant the same number of seeds from a population for each generation of inbreeding. Enough seeds are harvested to compensate for plants that did not germinate or produce seed.

Other common and less-common breeding methods are known and used in the art. See, e.g., R. W. Allard, Principles of Plant Breeding (John Wiley and Sons, Inc., New York, N.Y., 1967); N. W. Simmonds, Principles of Crop Improvement (Longman, London, 1979); J. Sneep et al., Plant Breeding Perspectives (Pudoc, Wageningen, 1979); and W. R. Fehr, Principles of Cultivar Development: Theory and Technique (Macmillian Publ., New York, N.Y., 1987).

Proper testing should detect any major faults and establish the level of superiority or improvement over current cultivars. In addition to showing superior performance, there must be a demand for a new cultivar that is compatible with industry standards or that creates a new market. The introduction of a new cultivar may incur additional costs to the seed producer, the grower, processor and consumer for such things as special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

In recent years, a few herbicide-tolerant rice varieties and hybrids have been successfully introduced to the market. See U.S. Pat. Nos. 5,545,822; 5,736,629; 5,773,703; 5,773,704; 5,952,553; and 6,274,796; and published International Patent Applications WO 00/27182 and WO 01/85970. These herbicide-tolerant rice plants are resistant to or tolerant of herbicides that normally inhibit the growth of rice plants. Thus, rice growers now can control weeds that previously were difficult to control in rice fields, including "red rice." "Red rice" is a weedy relative of cultivated rice, and had previously been difficult to control because it actually belongs to the same species as cultivated rice. Only when herbicide tolerant rice became available recently did it become possible to control red rice with herbicides in fields where cultivated rice was growing contemporaneously. However, there are currently only a very limited number of herbicide-tolerant cultivars and hybrids available commercially. There is a continuing need for new herbicide-tolerant cultivars and hybrids—that is, rice plants that not only express a desired herbicide-tolerant phenotype, but also possess other agronomically desirable characteristics. Additional herbicide-tolerant cultivars and hybrids will provide rice growers greater flexibility in planting and managing crops.

I have discovered a novel rice cultivar having superior straighthead and lodging resistance, superior processing characteristics, high grain yield characteristics, and early maturity as compared to other available long-grain cultivars. This invention is a new and distinct rice cultivar, designated 'Trenasse.' This invention also pertains to the seeds of rice cultivar 'Trenasse,' the plants of rice 'Trenasse,' and methods for producing a rice plant produced by crossing the rice variety 'Trenasse' with itself or another rice line. Thus any such methods using the rice variety 'Trenasse' are part of this invention, including selfing, backcrosses, hybrid production, and crosses to populations. All plants produced using the rice variety 'Trenasse' as a parent are also within the scope of this invention. This rice variety may also be used in crosses with other rice plants to produce first generation ($F_1$ hybrid cultivars) rice hybrid seeds and hybrid plants with superior characteristics.

In another embodiment, this invention allows for single-gene converted plants of 'Trenasse.' The single transferred gene may be a dominant or recessive allele. Preferably, the single transferred gene will confer, in addition to traits previously mentioned, traits such as herbicide resistance, insect resistance, resistance to bacterial, fungal or viral disease, male fertility, male sterility, enhanced nutritional quality, and industrial usage. The single gene may be a naturally occurring rice gene or a transgene introduced through genetic engineering techniques known in the art.

In another embodiment, this invention allows for regenerable cells for use in tissue culture of rice plant 'Trenasse.' The tissue culture may allow for regeneration of plants having physiological and morphological characteristics of rice plant 'Trenasse' and of regenerating plants having substantially the same genotype as rice plant 'Trenasse' as known in the art. Preferably, the regenerable cells in the tissue cultures will be embryos, protoplasts, meristematic cells, callus, pollen, leaves, anthers, root tips, flowers, seeds, panicles or stems. In addition, the invention allows for rice plants regenerated from the tissue cultures of the invention.

DEFINITIONS

The following definitions apply throughout the specification and claims, unless the context clearly indicates otherwise:

"Days to 50% heading." Average number of days from seeding to the day when 50% of all panicles are exerted at least partially through the leaf sheath. A measure of maturity.

"Grain Yield." Grain yield is measured in pounds per acre, at 12.0% moisture. Grain yield depends on a number of factors, including the number of panicles per unit area, the number of fertile florets per panicle, and grain weight per floret.

"Lodging Percent." Lodging is a subjectively measured rating, and is the percentage of plant stems leaning or fallen completely to the ground before harvest.

"Grain Length (L)." Length of a rice grain, or average length, measured in millimeters.

"Grain Width (W)." Width of a rice grain, or average width, measured in millimeters.

"Length/Width (L/W) Ratio." This ratio is determined by dividing the average length (L) by the average width (W).

"1000 Grain Wt." The weight of 1000 rice grains, measured in grams.

"Harvest Moisture." The percentage moisture in the grain when harvested.

"Plant Height." Plant height in centimeters, measured from soil surface to the tip of the extended panicle at harvest.

"Apparent Amylose Percent." The percentage of the endosperm starch of milled rice that is amylase. The apparent amylase percent is an important grain characteristic that affects cooking behavior. Standard long grains contain 20 to 23 percent amylose. Rexmont-type long grains contain 24 to 25 percent amylose. Short and medium grains contain 13 to 19 percent amylose. Waxy rice contains zero percent amylose. Amylose values, like most characteristics of rice, depend on the environment. "Apparent" refers to the procedure for determining amylose, which may also involve measuring some long chain amylopectin molecules that bind to some of the amylose molecules. These amylopectin molecules actually act similar to amylose in determining the relative hard or soft cooking characteristics.

"Alkali Spreading Value." An index that measures the extent of disintegration of the milled rice kernel when in contact with dilute alkali solution. An indicator of gelatinization temperature. Standard long grains have a 3 to 5 Alkali Spreading Value (intermediate gelatinization temperature).

"Peak Viscosity." The maximum viscosity attained during heating when a standardized, instrument-specific protocol is applied to a defined rice flour-water slurry.

"Trough Viscosity." The minimum viscosity after the peak, normally occurring when the sample starts to cool.

"Final Viscosity." Viscosity at the end of the test or cold paste.

"Breakdown." The peak viscosity minus the hot paste viscosity.

"Setback." Setback 1 is the final viscosity minus the trough viscosity. Setback 2 is the final viscosity minus the peak viscosity.

"RVA Viscosity." Viscosity, as measured by a Rapid Visco Analyzer, is a new but widely used laboratory instrument to examine paste viscosity or thickening ability of milled rice during the cooking process.

"Hot Paste Viscosity." Viscosity measure of rice flour/water slurry after being heated to 95° C. Lower values indicate softer and stickier cooking types of rice.

"Cool Paste Viscosity." Viscosity measure of rice flour/water slurry after being heated to 95° C. and uniformly cooled to 50° C. Values less than 200 indicate softer cooking types of rice.

"Allele." An allele is any of one or more alternative forms of the same gene. In a diploid cell or organism, the two alleles of a given gene occupy corresponding loci on a pair of homologous chromosomes.

"Backcrossing." Backcrossing is a process in which a breeder repeatedly crosses hybrid progeny back to one of the parents, for example, crossing a first generation hybrid $F_1$ with one of the parental genotypes of the $F_1$ hybrid, and then crossing a second generation hybrid $F_2$ with the same parental genotype, and so forth.

"Essentially all the physiological and morphological characteristics." A plant having "essentially all the physiological and morphological characteristics" of a specified plant refers to a plant having the same general physiological and morphological characteristics, except for those characteristics derived from a particular converted gene.

"Quantitative Trait Loci (QTL)." Quantitative trait loci (QTL) refer to genetic loci that to some degree control numerically measurable traits, generally traits that are continuously distributed.

"Regeneration." Regeneration refers to the development of a plant from tissue culture.

"Single Gene Converted (Conversion)." Single gene converted (conversion) includes plants developed by backcrossing wherein essentially all of the desired morphological and physiological characteristics of a parental variety are recovered, while retaining a single gene transferred into the variety via crossing and backcrossing. The term can also refer to the introduction of a single gene through genetic engineering techniques known in the art.

'Trenasse' is a very early, maturing, short stature, high yielding, long-grain rice variety that was developed at the Louisiana Agricultural Experiment Station (Rice Research Station) in Crowley, La., and tested under the experimental designation LA 2008. 'Trenasse' is an early selection from a cross-designated 96CR020, and has the pedigree 'Cypress'//L202/'Tebonnet'/3/LBLESC5. The parental pure lines are both experimental varieties that have not been released as commercial varieties. The female parent is 'Cypress'//L202/Tebennet. This line was tested in the Uniform Rice Regional Nursery ("URRN"; i.e., a multi-state testing program) with the experimental designation RU 9602103. This experimental line was developed from a cross of 'Cypress,''L202,' and 'Tebonnet.' 'Cypress' is an early, semidwarf, long-grain variety that was developed at the Rice Research Station. 'L202 is a semidwarf, very early, long grain variety that was developed at the Rice Experiment Station in Biggs, Calif. 'Tebonnet' is a tall, very early long grain developed at the Rice Research and Extension Center in Stuttgart The male parent (LBLESC5) is an advanced experimental long grain semidwarf line that was developed at the Rice Research Station. It was tested as an experimental variety in the URRN under the designation RU 9102146.

After the initial cross was made, the population was grown as five $F_1$ plants designated as 97T020. Seed from these plants was bulked and planted as $F_2$ plots designated as 8F7039. Two-hundred panicles were selected from the $F_2$ population and grown as panicle rows. Five panicles were selected from $F_3$ row, designated as 9925407, and planted as $F_4$ rows. Panicle row, which was designated as 0016184, was harvested as bulk seed (after 15 panicles were selected from the row). This panicle row was the basis for the variety 'Trenasse.' Seed from this bulked row was entered in a Preliminary Yield Test ("PY") as Entry PY619. The PY was reselected and entered into URRN tests as entry LA 0202008. The line was also entered into a Commercial-Advanced test (i.e., a multi-location testing program normally grown at between 6 to 9 locations in the Louisiana rice production area). The line was also grown as panicle rows and reselected and purified for two consecutive years. One thousand panicles were selected from a population of 15 panicle rows. The material was planted (as 800 panicle rows) at the Puerto Rico Winter Nursery, located near Lajas, Puerto Rico. This population was selected prior to harvest (139 rows were eliminated), and the bulked seed was returned to the Rice Research Station in Crowley, La. This seed was used to plant a 19.32 acre breeder/foundation field.

During each generation of headrow production, punitive or variant rows were removed from the field. Visual inspections of the headrows, including heading date, plant height, grain shape and size, phenotype, and plant color were used as criteria to confirm cultivar purity. Classes of seed will be breeder, foundation, registered, and certified. Foundation seed can be used to produce further foundation seed if necessary at the discretion of the breeder.

'Trenasse' has been observed in seed increase and production fields for three generations, and found to be uniform and stable, as described in the following variety description information. It has been increased with continued observation for uniformity.

Rice cultivar 'Trenasse' has the following morphologic and other characteristics (based primarily on data collected at Crowley, La.:

VARIETY DESCRIPTION INFORMATION

MATURITY (Crowley, La. at 165 kg N/ha):
Days to maturity (50% Heading): 74
6 days earlier than Cocodrie
Maturity Class (50% heading-Louisiana): Very Early (less then 80 days)
CULM: (Degrees from perpendicular after flowering)
Angle: Erect (less than 30 degrees)
Length: 104.1 cm (Soil level to top of extended panicle on main stem)
Taller than Cypress by 3.0 cm
Height Class: Short stature
Internode color (After flowering): Cream
Strength (Lodging resistance): Moderately strong
FLAG LEAF: (After Heading)
Length: 27 cm
Width: 10 mm
Pubescence: Glabrous
Leaf Angle (After heading): Erect
Blade Color: Green
Basal Leaf Sheath Color: Green
LIGULE:
Color (Late vegetative state): White
Shape: Acute to acuminate
Collar Color (Late vegetative stage): colorless
Auricle Color (Late vegetative stage): colorless
PANICLE:
Length: 27 cm
Type: Intermediate
Secondary Branching: Moderate
Exertion (near maturity): >95%
Axis: Droopy
Shattering: Low (3%)
Threshability: Easy
GRAIN (Spikelet):
Awns (After full heading): normally awnless, some short awns
Apiculus Color (at maturity): Pale purple
Stigma Color: White
Lemma and Palea Pubescence: Glabrous
Spikelet Sterility (at maturity): Highly fertile (>90%)
GRAIN (Seed):
Seed Coat Color: Light brown
Endosperm Type: Nonglutinous (nonwaxy)
Endosperm Translucency: Clear
Endosperm Chalkiness: Low (less than 10% of sample)
Scent: Nonscented
Shape Class (Length/width ratio):
Paddy—Long (3.4: 1 or greater)
Brown—Long (3.1:1 or greater)
Milled—Long (3.0:1 or greater)

Measurements:

|  | Length (mm) | Width (mm) | L/W Ratio | 1000 Grains (grams) |
|---|---|---|---|---|
| Rough | 9.3 | 2.67 | 3.5 | 25.05 |
| Brown | 7.19 | 2.32 | 3.11 | 20.65 |
| Milled | 6.7 | 2.23 | 3.01 | 19.0 |

Milling Yield (% whole kernel (head) rice to rough rice): 62.8%

Protein (NIR): 6.9

Amylose: 20.9

Alkali Spreading value: 4.1 (1.5% KOH Solution)

Gelatinization Temperature Type: Intermediate (4.1)

Amylographic Paste Viscosity (Rapid Visco Amylograph—RVU)

|  |  |
|---|---|
| Peak | 287.9 |
| Hot Paste | 155.3 |
| Cooled | 294.6 |

RESISTANCE TO LOW TEMPERATURE:

Germination and Seedling Vigor: Medium

Flowering (Spikelet fertility): Medium

SEEDLING VIGOR NOT RELATED TO LOW TEMPERATURE:

Vigor: Medium

DISEASE RESISTANCE:

Sheath Blight (*Rhizoctonia solani*): Susceptible

Leaf Blast (*Pyricularia grisea*): Moderately susceptible

Narrow Brown Leaf Spot (*Cercospora janseana*): Resistant

Leaf Smut (*Entyloma oryzae*): Moderately resistant

Brown Spot (*Cochiobolus miyabeanus*): Moderately resistant

Panicle Blight: Susceptible

STRAIGHTHEAD DISORDER: Moderately resistant

INSECT RESISTANCE: Rice Water Weevil (*Lissorhoptrus oryzophilus*):

Susceptible.

Table 1 shows the agronomic and grain quality performance of 'Trenasse,' 'Cheniere,' 'Cocodrie,' and 'Cypress' during trials over a three year period at Crowley, La.

This invention is also directed to methods for producing a rice plant by crossing a first parent rice plant with a second parent rice plant, wherein the first or second rice plant is a rice plant from the line 'Trenasse.' Further, both first and second parent rice plants may be from the cultivar 'Trenasse.' Therefore, methods using the cultivar 'Trenasse' are part of this invention, including selfing, backcrosses, hybrid breeding, and crosses to populations. Any plants produced using cultivar 'Trenasse' as a parent are within the scope of this invention.

This invention is also directed to methods for producing a hybrid rice plant by crossing a first parent rice plant with a second parent rice plant, wherein either the first or second parent rice plant is 'Trenasse.' Further, this invention also is directed to methods for producing a hybrid rice line derived from 'Trenasse' by crossing 'Trenasse' with a second rice plant, and growing the progeny seed. The crossing and growing steps may be repeated any number of times. Breeding methods using the rice line 'Trenasse' are considered part of this invention, not only backcrossing and hybrid production, but also selfing, crosses to populations, and other breeding methods known in the art.

If desired, either of the parents in such a cross, 'Trenasse' or the other parent, through techniques known in the art be produced in male-sterile form.

FURTHER EMBODIMENTS OF THE INVENTION

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, anthers and the like. Thus, another aspect of this invention is to provide for cells which upon growth and differentiation produce a cultivar having essentially all of the physiological and morphological characteristics of 'Trenasse.'

Techniques for transforming with and expressing desired structural genes and cultured cells are known in the art. Also, as known in the art, rice may be transformed and regenerated such that whole plants containing and expressing desired genes under regulatory control are obtained. General descriptions of plant expression vectors and reporter genes and transformation protocols can be found, for example, in Gruber et al., "Vectors for Plant Transformation, in Methods in Plant Molecular Biology & Biotechnology" in Glich et al. (Eds. pp. 89-119, CRC Press, 1993). For example, expression vectors and gene cassettes with the GUS reporter are

TABLE 1

| ID | Vigor[1] | Heading[2] | Height[3] | Lodging[4] | Yield[5] | Whole[6] | Total[7] |
|---|---|---|---|---|---|---|---|
| 'Trenasse' | 5 | 74 | 104.1 | 0 | 7217 | 62.8 | 68.8 |
| 'Cheniere' | 5 | 82 | 96.5 | 0 | 7358 | 66.5 | 72.3 |
| 'Cocodrie' | 4 | 80 | 96.5 | 0 | 7587 | 64.5 | 70.6 |
| 'Cypress' | 4 | 83 | 101.6 | 11 | 6782 | 67.1 | 71.3 |

[1]Subjective rating of seedling vigor - scale 1–9, with lower numbers indicating higher levels of vigor.
[2]Days from emergence to 50% heading.
[3]Plant height from soil line to tip of extended panicle on main stem.
[4]Lodging - Percentage of plant lodged at harvest maturity.
[5]Yield - in lb per acre, converted to 12% grain moisture.
[6]Milling - whole - (Percentage whole kernel (head) rice to rough rice).
[7]Milling - total - (Percentage total rice to rough rice).

available from Clone Tech Laboratories, Inc. (Palo Alto, Calif.), and expression vectors and gene cassettes with luciferase reporter are available from Pro Mega Corp. (Madison, Wis.). General methods of culturing plant tissues are provided, for example, by Maki et al., "Procedures for Introducing Foreign DNA into Plants" in Methods in Plant Molecular Biology & Biotechnology, Glich et al., (Eds. pp. 67-88 CRC Press, 1993); by Phillips et al., "Cell-Tissue Culture and In-Vitro Manipulation" in Corn & Corn Improvement, 3rd Edition; by Sprague. et al., (Eds. pp. 345-387) American Society of Agronomy Inc., 1988. Methods of introducing expression vectors into plant tissue include the direct infection or co-cultivation of plant cells with *Agrobacterium tumefaciens*, Horsch et al., *Science*, 227:1229 (1985). Descriptions of *Agrobacterium* vectors systems and methods for *Agrobacterium*-mediated gene transfer are provided by Gruber et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with biolistic device- or *Agrobacterium*-mediated transformation. Transformed plants obtained with the germplasm of 'Trenasse' are intended to be within the scope of this invention.

The present invention also provides rice plants regenerated from a tissue culture of the 'Trenasse' variety or hybrid plant. As is known in the art, tissue culture can be used for the in vitro regeneration of a rice plant. For example, see Chu, Q. R. et al. (1999) "Use of bridging parents with high anther culturability to improve plant regeneration and breeding value in rice," *Rice Biotechnology Quarterly*, 38:25-26; Chu, Q. R. et al., "A novel plant regeneration medium for rice anther culture of Southern U.S. crosses," *Rice Biotechnology Quarterly*, 35:15-16 (1998); Chu, Q. R. et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J Breed.*, 33 (Suppl.2), 306-307, illus. 1983, the complete disclosures of which are hereby incorporated by reference. Thus, another aspect of this invention is to provide cells, which upon growth and differentiation produce rice plants having all, or essentially all, of the physiological and morphological characteristics of variety 'Trenasse.'

Unless context clearly indicates otherwise, references in the specification and claims to 'Trenasse' should be understood also to include single gene conversions of 'Trenasse.' Traits that may be incorporated in single gene conversions include, for example, traits known in the art for such things as male sterility, sources of herbicide resistance, resistance for bacterial, fungal, or viral disease, insect resistance, male fertility, enhanced nutritional quality, industrial usage, yield stability and yield enhancement.

Duncan et al., *Planta*, 165:322-332 (1985) reflects that 97% of the plants cultured that produced callus were capable of plant regeneration. Subsequent experiments with both inbreds and hybrids produced 91% regenerable callus that produced plants. In a further study in 1988, Songstad et al., *Plant Cell Reports*, 7:262-265 (1988), reports several media additions that enhance regenerability of callus of two inbred lines. Other published reports also indicate that "nontraditional" tissues are capable of producing somatic embryogenesis and plant regeneration. K. P. Rao et al., *Maize Genetics Cooperation Newsletter*, 60:64-65 (1986), refers to somatic embryogenesis from glume callus cultures and B. V. Conger et a!., *Plant Cell Reports*, 6:345-347 (1987) indicates somatic embryogenesis from the tissue cultures of corn leaf segments. These methods of obtaining plants are routinely used with a high rate of success.

Tissue culture of corn is described in European Patent Application No. 160,390, incorporated herein by reference. Corn tissue culture procedures are also described in Green, et al., "Plant Regeneration in Tissue Culture of Maize," *Maize for Biological Research* (Plant Molecular Biology Association, Charlottesville, Va., pp. 367-372, 1982) and in Duncan et al., "The Production of Callus Capable of Plant Regeneration from Immature Embryos of Numerous *Zea Mays* Genotypes," 165 *Planta*, 322:332 (1985). Thus, another aspect of this invention is to provide cells, which upon growth and differentiation produce rice plants having all, or essentially all, of the physiological and morphological characteristics of hybrid rice line 'Trenasse.' T. P. Croughan, et al., (Springer-Verlag, Berlin, 1991) Rice (*Oryza sativa.* L): Establishment of Callus Culture and the regeneration of Plants, *In Biotechnology in Agriculture and Forestry*, (19-37).

With the advent of molecular biological techniques that allow the isolation and characterization of genes that encode specific protein products, it is now possible to routinely engineer plant genomes to contain and express foreign genes, or additional, or modified versions of native, or endogenous, genes (perhaps driven by different promoters) in order to alter the traits of a plant in a specific manner. Such foreign, additional, and modified genes are herein referred to collectively as "transgenes." Over the last 15 to 20 years, several methods for producing transgenic plants have been developed, and the present invention, in particular embodiments, also relates to transformed versions of 'Trenasse.'

An expression vector is constructed that will function in plant cells. Such a vector comprises a DNA coding sequence under the control of or operatively linked to a regulatory element (e.g., a promoter). The expression vector may contain one or more such operably linked coding sequence/regulatory element combinations. The vector(s) may be in the form of a plasmid, and can be used alone or in combination with other plasmids, to provide transformed rice plants.

Expression Vectors

Expression vectors commonly include at least one genetic "marker," operably linked to a regulatory element (e.g., a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are known in the art, and include, for example, genes that code for enzymes that metabolically detoxify a selective chemical inhibitor such as an antibiotic or a herbicide, or genes that encode an altered target which is insensitive to such an inhibitor. Positive selection methods are also known in the art.

For example, a commonly used selectable marker gene for plant transformation is that for neomycin phosphotransferase II (nptII), isolated from transposon Tn5, whose expression confers resistance to kanamycin. See Fraley et al., *Proc. Natl. Acad. Sci. U.S.A.*, 80:4803 (1983). Another commonly used selectable marker gene is the hygromycin phosphotransferase gene, which confers resistance to the antibiotic hygromycin. See Vanden Elzen et al., *Plant Mol. Biol.*, 5:299 (1985).

Additional selectable marker genes of bacterial origin that confer resistance to one or more antibiotics include gentamycin acetyl transferase, streptomycin phosphotransferase, aminoglycoside-3'-adenyl transferase, the bleomycin resistance determinant. Hayford et al., *Plant Physiol.*, 86:1216 (1988), Jones et al., *Mol. Gen. Genet.*, 210:86 (1987), Svab et al., *Plant Mol. Biol.*, 14:197 (1990); *Plant Mol. Biol.*, 7:171 (1986). Other selectable marker genes confer resistance to herbicides such as glyphosate, glufosinate, or broxynil. Comai et al., *Nature*, 317:741-744 (1985); Gordon-Kamm et al., *Plant Cell*, 2:603-618 (1990); and Stalker et al., *Science*, 242:419-423 (1988).

Selectable marker genes for plant transformation of non-bacterial origin include, for example, mouse dihydrofolate reductase, plant 5-enolpyruvylshikimate-3-phosphate synthase, and plant acetolactate synthase. Eichholtz et al., *Somatic Cell Mol. Genet.* 13:67 (1987); Shah et al., *Science*, 233:478 (1986); and Charest et al., *Plant Cell Rep.*, 8:643 (1990).

Another class of marker genes for plant transformation employs screening of presumptively transformed plant cells, rather than selection for resistance to a toxic substance such as an antibiotic. These marker genes are particularly useful to quantify or visualize the spatial pattern of expression of a gene in specific tissues, and are frequently referred to as reporter genes because they may be fused to the target gene or regulatory sequence. Commonly used reporter genes include glucuronidase (GUS), galactosidase, luciferase, chloramphenicol, and acetyltransferase. See Jefferson, R. A., *Plant Mol. Biol. Rep.*, 5:387 (1987); Teeri et al., *EMBO J.*, 8:343 (1989); Koncz et al., *Proc. Natl. Acad. Sci. U.S.A.*, 84:131 (1987); and DeBlock et al., *EMBO J.*, 3:1681 (1984). Another approach to identifying relatively rare transformation events has been the use of a gene that encodes a dominant constitutive regulator of the *Zea mays* anthocyanin pigmentation pathway. Ludwig et al., *Science*, 247:449 (1990).

The Green Fluorescent Protein (GFP) gene has been used as a marker for gene expression in prokaryotic and eukaryotic cells. See Chalfie et al., *Science*, 263:802 (1994). GFP and mutants of GFP may be used as screenable markers.

Genes included in expression vectors are driven by a nucleotide sequence comprising a regulatory element, for example, a promoter. Many suitable promoters are known in the art, as are other regulatory elements that may be used either alone or in combination with promoters.

As used herein, "promoter" refers to a region of DNA upstream from the transcription initiation site, a region that is involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters are examples of "non-constitutive" promoters. A "constitutive" promoter is a promoter that is generally active under most environmental conditions.

A. Inducible Promoters

An inducible promoter is operably-linked to a gene for expression in rice. Optionally, the inducible promoter is operably-linked to a nucleotide sequence encoding a signal sequence which is operably linked to a gene for expression in rice. With an inducible promoter the rate of transcription increases in response to an inducing agent.

Any suitable inducible promoter may be used in the present invention. See Ward et al., *Plant Mol. Biol.*, 22:361-366 (1993). Examples include those from the ACEI system, which responds to copper (Meft et al., *PNAS*, 90:4567-4571 (1993)); In2 gene from maize, which responds to benzenesulfonamide herbicide safeners (Hershey et al., *Mol. Gen Genetics*, 227:229-237 (1991) and Gatz; et al., *Mol. Gen. Genetics*, 243:32-38 (1994)); and Tet repressor from Tn10 (Gatz, *Mol. Gen. Genetics*, 227:229-237 (1991)). A preferred inducible promoter is one that responds to an inducing agent to which plants do not normally respond, for example, the inducible promoter from a steroid hormone gene, the transcriptional activity of which is induced by a glucocorticosteroid hormone. See Schena et al., *Proc. Natl. Acad. Sci.*, U.S.A. 88:0421 (1991).

B. Constitutive Promoters

A constitutive promoter is operably linked to a gene for expression in rice, or the constitutive promoter is operably linked to a nucleotide sequence encoding a signal sequence that is operably linked to a gene for expression in rice.

Constitutive promoters may also be used in the instant invention. Examples include promoters from plant viruses such as the 35S promoter from cauliflower mosaic virus (Odell et al., *Nature*, 313:810-812 (1985), and the promoters from the rice actin gene (McElroy et al., *Plant Cell*, 2:163-171 (1990)); ubiquitin (Christensen et al., *Plant Mol. Biol.*, 12:619-632 (1989) and Christensen et al., *Plant Mol. Biol.* 18:675-689 (1992)); pEMU (Last et al., *Theor. Appl. Genet.*, 81:581-588 (1991)); MAS (Velten et al., *EMBO J.*, 3:2723-2730 (1984)); and maize H3 histone (Lepetit et al., *Mol. Gen. Genetics*, 231:276-285 (1992). and Atanassova et al., *Plant Journal*, 2 (3): 291-300 (1992)).

An ALS promoter, such as the Xba1/NcoI fragment 5' from the *Brassica napus* ALS3 structural gene (or a nucleotide sequence similar to said Xba1/NcoI fragment), may be used as a constitutive promoter. See PCT Application WO96/30530. The promoter from a rice ALS (AHAS) gene may also be used. See the sequences disclosed in PCT Application WO 01/85970.

C. Tissue-Specific or Tissue-Preferred Promoters

A tissue-specific promoter is operably linked to a gene for expression in rice. Optionally, the tissue-specific promoter is operably linked to a nucleotide sequence encoding a signal sequence that is operably-linked to a gene for expression in rice. Transformed produce the expression product of the transgene exclusively, or preferentially, in specific tissue(s).

Any tissue-specific or tissue-preferred promoter may be used in the instant invention. Examples of tissue-specific or tissue-preferred promoters include those from the phaseolin gene (Murai et al., *Science*, 23:476-482 (1983) and Sengupta-Gopalan et al., *Proc. Natl. Acad. Sci. U.S.A.*, 82:3320-3324 (1985)); a leaf-specific and light-induced promoter such as that from cab or rubisco (Simpson et al., *EMBO J.*, 4(11):2723-2729 (1985) and Timko et al., *Nature*, 318:579-582 (1985)); an anther-specific promoter such as that from LAT52 (Twell et al., *Mol. Gen. Genetics*, 217:240-245 (1989)); a pollen-specific promoter such as that from Zm13 (Guerrero et al., *Mol. Gen. Genetics*, 244:161-168 (1993));

or a microspore-preferred promoter such as that from apg (Twell et al., *Sex. Plant Reprod.*, 6:217-224 (1993)).

Signal Sequences for Targeting Proteins to Subcellular Compartments

Transport of protein or peptide molecules produced by transgenes to a subcellular compartment such as a chloroplast, vacuole, peroxisome, glyoxysome, cell wall or mitochondrion, or for secretion into an apoplast, is accomplished by operably linking a nucleotide sequence encoding a signal sequence to the 5' or 3' end of a gene encoding the protein or peptide of interest. Targeting sequences at the 5' or 3' end of the structural gene may determine, during protein synthesis and processing, where the encoded protein is ultimately compartmentalized.

Many signal sequences are known in the art. See, for example, Becker et al.,. *Plant Mol. Biol.*, 20:49 (1992); Close, P. S., Master's Thesis, Iowa State University (1993); Knox, C. et al., "Structure and Organization of Two Divergent Alpha-Amylase Genes from Barley," *Plant Mol. Biol.*, 9:3-17 (1987); Lemer et al., *Plant Physiol.*, 91:124-129 (1989); Fontes et al., *Plant Cell*, 3:483-496 (1991); Matsuoka et al., *Proc. Natl. Acad. Sci.*, 88:834 (1991), Gould et al., *J Cell. Biol.*, 108:1657 (1989); Creissen et al., *Plant J.*, 2:129 (1991); Kalderon et al., "A short amino acid sequence able to specify nuclear location," *Cell*, 39:499-509 (1984); and Steifel et al., "Expression of a maize cell wall hydroxyproline-rich glycoprotein gene in early leaf and root vascular differentiation," *Plant Cell*, 2:785-793 (1990).

Foreign Protein Genes and Agronomic Genes

Agronomically significant genes that may be transformed into rice plants in accordance with the present invention include, for example, the following:

1. Genes that Confer Resistance to Pests or Disease:
   A. Plant disease resistance genes. Plant defenses are often activated by specific interaction between the product of a disease resistance gene (R) in the plant and the product of a corresponding avirulence (Avr) gene in the pathogen. A plant may be transformed with a cloned resistance gene to engineer plants that are resistant to specific pathogen strains. See, e.g., Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); and Mindrinos et al., *Cell* 78:1089 (1994) (*Arabidopsis* RSP2 gene for resistance to *Pseudomonas syringae*).
   B. A *Bacillus thuringiensis* protein, a derivative thereof or a synthetic polypeptide modeled thereon. See, e.g., Geiser et al., Gene 48:109 (1986), disclosing the cloning and nucleotide sequence of a Bt-endotoxin gene. DNA molecules encoding endotoxin genes may be obtained from American Type Culture Collection, Manassas, Va., for example, under ATCC Accession Nos. 40098, 67136, 31995, and 31998.
   C. A lectin. See, e.g., Van Damme et al., *Plant Molec. Biol.* 24:25 (1994), disclosing the nucleotide sequences of several *Clivia miniata* mannose-binding lectin genes.
   D. A vitamin-binding protein such as avidin. See PCT Application US93/06487, the contents of which are hereby incorporated by reference. The application teaches the use of avidin and avidin homologues as larvicides against insect pests.
   E. An enzyme inhibitor, for example, a protease or proteinase inhibitor or an amylase inhibitor. See, e.g., Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor 1); and Sumitani et al., *Biosci. Biotech. Biochem.* 57:1243 (1993) (nucleotide sequence of Streptomyces nitrosporeus-amylase inhibitor).
   F. An insect-specific hormone or pheromone such as an ecdysteroid and juvenile hormone, a variant thereof, a mimetic based thereon, or an antagonist or agonist thereof. See, e.g., Hammock et al., *Nature*, 344:458 (1990), disclosing baculovirus expression of cloned juvenile hormone esterase, an inactivator of juvenile hormone.
   G. An insect-specific peptide or neuropeptide that, upon expression, disrupts the physiology of the affected pest. See, e.g., Regan, *J. Biol. Chem.* 269:9 (1994) (expression cloning yields DNA coding for insect diuretic hormone receptor); and Pratt et al., *Biochem. Biophys. Res. Comm.*, 163:1243 (1989) (an allostatin in *Diploptera puntata*). See also U.S. Pat. No. 5,266,317 to Tomalski et al., disclosing genes encoding insect-specific, paralytic neurotoxins.
   H. An insect-specific venom produced in nature by a snake, a wasp, etc. For example, see Pang et al., *Gene*, 116:165 (1992), concerning heterologous expression in plants of a gene coding for a scorpion insectotoxic peptide.
   I. An enzyme responsible for a hyperaccumulation of a monoterpene, a sesquiterpene, a steroid, hydroxamic acid, a phenylpropanoid derivative or another non-protein molecule with insecticidal activity.
   J. An enzyme involved in the modification, including post-translational modification, of a biologically active molecule; e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application WO 9302197 to Scott et al., which discloses the nucleotide sequence of a callase gene. DNA molecules which contain chitinase-encoding sequences can be obtained, for example, from the American Type Culture Collection under Accession Nos. 39637 and 67152. See also Kramer et al., *Insect Biochem. Molec. Biol.* 23:691 (1993), which discloses the nucleotide sequence of a cDNA encoding tobacco hookworm chitinase; and Kawalleck et al., *Plant Molec. Biol.*, 21:673 (1993), which discloses the nucleotide sequence of the parsley ubi4-2 polyubiquitin gene.
   K. A molecule that stimulates signal transduction. See, e.g., Botella et al., *Plant Molec. Biol.*, 24:757 (1994), which discloses nucleotide sequences for mung bean calmodulin cDNA clones; and Griess et al., *Plant Physiol.*, 104:1467 (1994), which discloses the nucleotide sequence of a maize calmodulin cDNA clone.
   L. An antimicrobial or amphipathic peptide. See PCT Application WO9516776 (disclosing peptide derivatives of Tachyplesin that inhibit fungal plant pathogens); and PCT Application WO9518855 (disclosing synthetic antimicrobial peptides that confer disease resistance), the respective contents of which are hereby incorporated by reference.
   M. A membrane permease, a channel former or a channel blocker. See, e.g., Jaynes et al., *Plant Sci.*, 89:43 (1993), which discloses heterologous expression of a cecropin lytic peptide analog to render transgenic tobacco plants resistant to *Pseudomonas solanacearum*.

N. A viral-invasive protein or a complex toxin derived therefrom. For example, the accumulation of viral coat proteins in transformed plant cells induces resistance to viral infection or disease development caused by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. See Beachy et al., *Ann. Rev. Phytopathol.*, 28:451 (1990).

O. An insect-specific antibody or an immunotoxin derived therefrom. Thus, an antibody targeted to a critical metabolic function in the insect gut inactivates an affected enzyme, killing the insect. See Taylor et al., Abstract #497, Seventh Int'l Symposium on Molecular Plant-Microbe Interactions (Edinburgh, Scotland, 1994) (enzymatic inactivation in transgenic tobacco via production of single-chain antibody fragments).

P. A virus-specific antibody. See, e.g., Tavladoraki et al., *Nature*, 366:469 (1993), showing protection of transgenic plants expressing recombinant antibody genes from virus attack.

Q. A developmental-arrest protein produced in nature by a pathogen or a parasite. For example, fungal endo-1, 4-D-polygalacturonases facilitate fungal colonization and plant nutrient release by solubilizing plant cell wall homo-1,4-D-galacturonase. See Lamb et al., *Bio/Technology*, 10:1436 (1992). The cloning and characterization of a gene that encodes a bean endopolygalacturonase-inhibiting protein is described by Toubart et al., *Plant J.*, 2:367 (1992).

R. A developmental-arrest protein produced in nature by a plant. For example, Logemann et al., *Bio/Technology*, 10:305 (1992) reported that transgenic plants expressing the barley ribosome-inactivating gene have an increased resistance to fungal disease.

2. Genes that Confer Resistance to a Herbicide, for Example:

A. A herbicide that inhibits the growing point or meristem, such as an imidazolinone or a sulfonylurea. Exemplary genes in this category code for mutant ALS and AHAS enzyme as described, for example, by Lee et al., *EMBO J*, 7:1241 (1988); and Miki et al., *Theor. Appl. Genet.*, 80:449 (1990), respectively. See, additionally, U.S. Pat. Nos. 5,545,822; 5,736,629; 5,773, 703; 5,773,704; 5,952,553; and 6,274,796; and Published International Patent Applications WO 00/27182 and WO 01/85970. Resistance to AHAS-acting herbicides may be through a mechanism other than a resistant AHAS enzyme. See, e.g., U.S. Pat. No. 5,545,822.

B. Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cyclohexones (ACCase inhibitor-encoding genes). See, e.g., U.S. Pat. No. 4,940,835 to Shah et al., which discloses the nucleotide sequence of a form of EPSP which confers glyphosate resistance. A DNA molecule encoding a mutant aroA gene can be obtained under ATCC Accession Number 39256, and the nucleotide sequence of the mutant gene is disclosed in U.S. Pat. No. 4,769,061 to Comai. European Patent Application No. 0333033 to Kumada et al.; and U.S. Pat. No. 4,975,374 to Goodman et al., disclose nucleotide sequences of glutamine synthetase genes that confer resistance to herbicides such as L-phosphinothricin. The nucleotide sequence of a phosphinothricin-acetyl-transferase gene is provided in European Application No. 0242246 to Leemans et al. and DeGreef et al., *Bio/Technology*, 7:61 (1989), describing the production of transgenic plants that express chimeric bar genes coding for phosphinothricin acetyl transferase activity. Examples of genes conferring resistance to phenoxy propionic acids and cyclohexones, such as sethoxydim and haloxyfop, are the Acc1-S1, Acc1-S2, and Acc1-S3 genes described by Marshall et al., *Theor. Appl. Genet.*, 83:435 (1992).

C. A herbicide that inhibits photosynthesis, such as a triazine (psbA and gs+ genes) or a benzonitrile (nitrilase gene). Przibilla et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.*, 285:173 (1992).

3. Genes that Confer or Contribute to a Value-added Trait, such as:

A. Modified fatty acid metabolism, for example, by transforming a plant with an. antisense sequence to stearyl-ACP desaturase, to increase stearic acid content-of the plant. See Knultzon et al., *Proc. Natl. Acad. Sci. U.S.A.* 89:2624 (1992).

B. Decreased Phytate Content

1) Introduction of a phytase-encoding gene would enhance breakdown of phytate, adding more free phosphate to the transformed plant. See, for example, Van Hartingsveldt et al., *Gene*, 127:87 (1993), disclosing the nucleotide sequence of an *Aspergillus niger* phytase gene.

2) A gene may be introduced to reduce phytate content. For example, this may be accomplished by cloning, and then reintroducing DNA associated with an allele that is responsible for maize mutants characterized by low levels of phytic acid, a homologous or analogous mutation in rice may be used. See Raboy et al., *Maydica*, 35:383 (1990).

C. Carbohydrate composition may be modified, for example, by transforming plants with a gene coding for an enzyme that alters the branching pattern of starch. See Shiroza et al., *J. Bacteol.*, 170:810 (1988) (nucleotide sequence of *Streptococcus* mutant fructosyltransferase gene); Steinmetz et al., *Mol. Gen. Genet.*, 20:220 (1985) (nucleotide sequence of *Bacillus subtilis* levansucrase gene); Pen et al., *Bio/Technology*, 10:292 (1992) (production of transgenic plants that express *Bacillus licheniformis* amylase); Elliot et al., *Plant Molec. Biol.*, 21:515 (1993) (nucleotide sequences of tomato invertase genes); Søgaard et al., *J Biol. Chem.*, 268:22480 (1993) (site-directed mutagenesis of barley amylase gene); and Fisher et al., *Plant Physiol.*, 102:1045 (1993) (maize endosperm starch branching enzyme 11).

Methods for Rice Transformation

Numerous methods for plant transformation are known in the art, including both biological and physical transformation protocols. See, e.g., Miki, et al., "Procedures for Introducing Foreign DNA into Plants" in *Methods in Plant Molecular Biology and Biotechnology*; Glick B. R. and Thompson, J. E. (Eds.) (CRC Press, Inc., Boca Raton, 1993), pp. 67-88. In addition, expression vectors and in vitro culture methods for plant cell or tissue transformation and regeneration of plants are known in the art. See, e.g., Gruber et al., "Vectors for Plant Transformation" in Methods in *Plant Molecular Biology and Biotechnology*, Glick B. R. and Thompson, J. E. (Eds.) (CRC Press, Inc., Boca Raton, 1993), pp. 89-119.

A. *Agrobacterium*-Mediated Transformation

One method for introducing an expression vector into plants is based on the natural transformation system of *Agrobacterium*. See, e.g., Horsch et al., *Science*, 227:1229 (1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of plants. See, e.g., Kado, C. I., *Crit. Rev. Plant Sci.*, 10:1 (1991). Descriptions of *Agrobacterium* vector systems and methods for *Agrobacterium*-mediated gene transfer are provided by Gruber et al., supra; Miki et al., supra; and Moloney, et al., *Plant Cell Reports*, 8:238 (1989). See also U.S. Pat. No. 5,591,616.

B. Direct Gene Transfer

Despite the fact the host range for *Agrobacterium*-mediated transformation is broad, it is more difficult to transform some cereal crop species and gymnosperms via this mode of gene transfer, although success has been achieved in both rice and corn. See Hiei et al., *The Plant Journal*, 6:271-282 (1994); and U.S. Pat. No. 5,591,616. Other methods of plant transformation exist as alternatives to *Agrobacterium*-mediated transformation.

A generally applicable method of plant transformation is microprojectile-mediated (so-called "gene gun") transformation in which DNA is carried on the surface of microprojectiles, typically measuring 1 to 4 µm in diameter. The expression vector is introduced into plant tissues with a biolistic device that accelerates the microprojectiles to typical speeds of 300 to 600 m/s, sufficient to penetrate plant cell walls and membranes. Sanford et al., *Part. Sci. Technol.*, 5:27 (1987); Sanford, J. C., *Trends Biotech.*, 6:299 (1988); Klein et al., *Bio/Technology*, 6:559-563 (1988); Sanford, J. C., *Physiol Plant*, 7:206 (1990); and Klein et al., *Biotechnology*, 10:268 (1992). Various target tissues may be bombarded with DNA-coated microprojectiles to produce transgenic plants, including, for example, callus (Type I or Type II), immature embryos, and meristematic tissue.

Another method for physical delivery of DNA to plants is sonication of target cells. Zhang et al., *Bio/Technology*, 9:996 (1991). Alternatively, liposome or spheroplast fusion has been used to introduce expression vectors into plants. Deshayes et al., *EMBO J.*, 4:2731 (1985); and Christou et al., *Proc Natl. Acad. Sci.* U.S.A., 84:3962 (1987). Direct uptake of DNA into protoplasts, using $CaCl_2$ precipitation, polyvinyl alcohol or poly-L-ornithine, has also been reported. Hain et al., *Mol. Gen. Genet.*, 199:161 (1985); and Draper et al., *Plant Cell Physiol.*, 23:451 (1982). Electroporation of protoplasts and whole cells and tissues has also been described. Donn et al., in Abstracts of VIIth International Congress on Plant Cell and Tissue Culture IAPTC, A2-38, p. 53 (1990); D'Halluin et al., *Plant Cell*, 4:1495-1505 (1992); and Spencer et al., *Plant Mol. Biol.*, 24:51-61 (1994).

Following transformation of rice target tissues, expression of a selectable marker gene allows preferential selection of transformed cells, tissues, or plants, using regeneration and selection methods known in the art.

These methods of transformation may be used for producing a transgenic inbred line. The transgenic inbred line may then be crossed, with another inbred line (either transformed or non-transformed) line, to produce a new transgenic inbred line. Alternatively, a genetic trait that has been engineered into a particular rice line may be moved into another line using traditional backcrossing techniques. For example, backcrossing may be used to move an engineered trait from a public, non-elite inbred line into an elite inbred line, or from an inbred line containing a foreign gene in its genome into an inbred line or lines that do not contain that gene.

The term "inbred rice plant" should be understood also to include single gene conversions of an inbred line. Backcrossing methods can be used with the present invention to improve or introduce a characteristic into an inbred line.

Many single gene traits have been identified that are not regularly selected for in the development of a new inbred but that can be improved by backcrossing techniques. Single gene traits may or may not be transgenic. Examples of these traits include male sterility, waxy starch, herbicide resistance, resistance for bacterial, fungal, or viral disease, insect resistance, male fertility, enhanced nutritional quality, yield stability, and yield enhancement. These genes are generally inherited through the nucleus. Some known exceptions to this are the genes for male sterility, some of which are inherited cytoplasmically, but still act functionally as single gene traits. Several of these single gene traits are described in U.S. Pat. Nos. 5,777,196; 5,948,957; and 5,969,212; the disclosures of which are specifically hereby incorporated by reference.

DEPOSIT INFORMATION

Samples of the proprietary rice cultivar designated 'Trenasse,' have been deposited with the American Type Culture Collection (ATCC), 10801 University Boulevard, Manassas, Va. 20110-2209 on Jun. 30, 2005; and were assigned ATCC Accession No. PTA-6825. The deposit was made pursuant to a contract between ATCC and the assignee of this patent application, Board of Supervisors of Louisiana State University and Agricultural and Mechanical College. The contract with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for the availability of these seeds to one determined by the U.S. Commissioner of Patents and Trademarks (or by any counterpart to the Commissioner in any patent office in any other country) to be entitled thereto under pertinent statutes and regulations. The assignee of the present application has agreed that if any of the seeds on deposit should become nonviable or be lost or destroyed when cultivated under suitable conditions, they will be promptly replaced on notification with a viable sample of the same seeds.

The complete disclosures of all references cited in this specification are hereby incorporated by reference. In the event of an otherwise irreconcilable conflict, however, the present specification shall control.

I claim:

1. A rice seed designated 'Trenasse,' wherein a representative sample of said seed has been deposited under ATCC Accession No. PTA-6825.

2. A plant, or a part thereof, produced by growing the seed of claim 1.

3. Pollen of the plant of claim 2.

4. An ovule of the plant of claim 2.

5. A rice plant, or a part thereof, having all of the physiological and morphological characteristics of the rice plant of claim 2.

6. A tissue culture of regenerable cells or protoplasts produced from the rice plant of claim 2.

7. The tissue culture of claim 6, wherein the cells of the tissue culture or protoplasts of the tissue culture are produced from a tissue selected from the group consisting of embryos, meristematic cells, pollen, leaves, anthers, roots, root tips, flowers, seeds, and stems.

8. A rice plant regenerated from the tissue culture of claim 7, said rice plant having all of the morphological and physiological characteristics of 'Trenasse.'

9. A method for producing an $F_1$ hybrid rice seed, said method comprising crossing a first parent rice plant with a second parent rice plant, and harvesting the resultant $F_1$ hybrid rice seed, wherein the first parent rice plant or the second parent rice plant is the rice plant of claim 2.

10. The method of claim 9, additionally comprising the step of planting a plurality of the $F_1$ hybrid rice seed under conditions favorable for the growth of rice plants.

11. A method as recited in claim 9, additionally comprising the step of harvesting rice seed produced by the resulting rice plants.

12. A method of producing a rice plant with enhanced herbicide resistance, said method comprising transforming the rice plant of claim 2 with a transgene that confers herbicide resistance.

13. A herbicide resistant rice plant produced by the method of claim 12.

14. A method of producing an insect resistant rice plant, said method comprising transforming the rice plant of claim 2 with a transgene that confers insect resistance.

15. An insect resistant rice plant produced by the method of claim 14.

16. A method of producing a disease resistant rice plant, said method comprising transforming the rice plant of claim 2 with a transgene that confers disease resistance.

17. A disease resistant rice plant produced by the method of claim 16.

18. A method of producing a rice plant with modified fatty acid or carbohydrate metabolism, said method comprising transforming the rice plant of claim 2 with one or more transgenes encoding a protein selected from the group consisting of fructosyltransferase, levansucrase, alpha-amylase, invertase, and starch branching enzyme; or encoding an antisense sequence to stearyl-ACP desaturase.

19. A rice plant having modified fatty acid or carbohydrate metabolism produced by the method of claim 18.

20. A method of introducing a desired trait into rice cultivar 'Trenasse' wherein the method comprises:
   (a) crossing 'Trenasse' plants, representative seed of which is deposited under ATCC Accession No. PTA-6825, with plants of another rice line that comprise the desired trait to produce $F_1$ progeny plants; wherein the desired trait is selected from the group consisting of male sterility, herbicide resistance, insect resistance and resistance to bacterial, fungal, or viral disease;
   (b) selecting $F_1$ progeny plants that have the desired trait to produce selected $F_1$ progeny plants;
   (c) crossing the selected $F_1$ progeny plants with the 'Trenasse' plants to produce first backcross progeny plants;
   (d) selecting for first backcross progeny plants that have both the desired trait and the physiological and morphological characteristics of rice cultivar 'Trenasse' to produce selected first backcross progeny plants; and
   (e) repeating steps (c) and (d) three or more times in succession to produce selected fourth or higher generation backcross progeny plants that comprise both the desired trait and all of the physiological and morphological characteristics of rice cultivar 'Trenasse' as described in the VARIETY DESCRIPTION INFORMATION and as determined at a 5% significance level when grown in the same environmental conditions.

21. A plant produced by the method of claim 20, wherein the plant has the desired trait and all of the physiological and morphological characteristics of rice cultivar 'Trenasse' as described in the VARIETY DESCRIPTION INFORMATION and as determined at a 5% significance level when grown in the same environmental conditions.

22. A method for producing rice plants, said method comprising planting a plurality of rice seeds as recited in claim 1 under conditions favorable for the growth of rice plants.

23. The method as recited in claim 22, additionally comprising the step of harvesting rice seed produced by the resulting rice plants.

* * * * *